United States Patent
Stamets

(10) Patent No.: US 11,471,450 B2
(45) Date of Patent: Oct. 18, 2022

(54) PSILOCYBIN COMPOSITIONS

(71) Applicant: Paul Edward Stamets, Shelton, WA (US)

(72) Inventor: Paul Edward Stamets, Shelton, WA (US)

(73) Assignee: TURTLE BEAR HOLDINGS, LLC, Shelton, WA (US)

(*) Notice: Subject to any disclaimer, the term of this patent is extended or adjusted under 35 U.S.C. 154(b) by 142 days.

(21) Appl. No.: 16/285,457

(22) Filed: Feb. 26, 2019

(65) Prior Publication Data

US 2019/0192498 A1 Jun. 27, 2019

Related U.S. Application Data

(60) Division of application No. 16/211,281, filed on Dec. 6, 2018, which is a continuation of application No. 15/494,503, filed on Apr. 23, 2017, now abandoned.

(60) Provisional application No. 62/365,982, filed on Jul. 23, 2016.

(51) Int. Cl.
*A61K 31/455* (2006.01)
*A61K 31/4045* (2006.01)
*A61K 31/675* (2006.01)
*A61K 36/07* (2006.01)

(52) U.S. Cl.
CPC ........ *A61K 31/455* (2013.01); *A61K 31/4045* (2013.01); *A61K 31/675* (2013.01); *A61K 36/07* (2013.01)

(58) Field of Classification Search
CPC .. A61K 31/35; A61K 31/455; A61K 31/4045; A61K 31/675; A61K 31/352; A61K 36/07
See application file for complete search history.

(56) References Cited

U.S. PATENT DOCUMENTS

| | | | |
|---|---|---|---|
| 3,075,992 A | 1/1963 | Hofmann et al. | |
| 3,078,214 A | 2/1963 | Hofmann et al. | |
| 3,192,111 A | 6/1965 | Hofmann et al. | |
| 2001/0008641 A1 | 7/2001 | Krotzer | |
| 2011/0038958 A1 | 2/2011 | Kikuchi et al. | |
| 2014/0220150 A1* | 8/2014 | Stamets | A61K 36/07 424/537 |
| 2016/0206670 A1 | 7/2016 | Wieser et al. | |
| 2018/0021326 A1 | 1/2018 | Stamets | |
| 2019/0105313 A1 | 4/2019 | Stamets | |
| 2019/0142851 A1 | 5/2019 | Chadeayne | |

FOREIGN PATENT DOCUMENTS

| | | |
|---|---|---|
| WO | 2005039546 A2 | 5/2005 |
| WO | 2006091988 A1 | 8/2006 |
| WO | 2008062983 A1 | 5/2008 |
| WO | 2016001922 A1 | 1/2016 |
| WO | 2020181194 A1 | 9/2020 |
| WO | 2021041407 A1 | 3/2021 |
| WO | 2021188812 A1 | 9/2021 |

OTHER PUBLICATIONS

"Biei et al., "Simultaneous Production of Psilocybin and a Cocktail of β-Carboline Monoamine Oxidase Inhibitors in Magic' Mushrooms," Chem. Eur. J. 10.1002/chem.201904363 accepted manuscript (2019).".
Jackowski, "Neural injury repair: hope for the future as barriers to effective CNS regeneration become clearer," Brittish J. of Neurosurgery, 1995, 9:303-317.
Ly et al., "Psychedelics Promote Structural and Functional Neural Plasticity," Cell Rep., 2018, 23: 3170-3182.
Rambousek et al., "The effect of psilocin on memory acquisition, retrieval, and consolidation in the rat," Frontiers in Behavioral Neuroscience, 2014, 8:1-7.
"Amount of niacin in mushrooms," <http://dietandfitnesstoday.com/niacin-in-mushrooms.php> May 28, 2019.
Schartner et al., "Increased spontaneous MEG signal diversity for psychoactive doses of ketamine, LSD and psilocybin," Nature Sci Reports, 7:46421 (2017).
Phan et al., "Edible and Medicinal Mushrooms: Emerging Brain Food for the Mitigation of Neurodegenerative Diseases," J Medicinal Foods 20(1): 1-10 (2017).
Passie et al., "The Pharmacology of Psilocybin," Addiction Biol. 7:357-364 (2002).
Atlow et al., "Effects of psilocybin on hippocampal neurogenesis and extinction of trace fear conditioning," Exp. Brain Res. 228: 481-491 (2013).
Friedman et al., "Chemistry, Nutrition, and Health-Promoting Properties of *Hericium ennaceus* (Lion's Mane) Mushroom Fruiting Bodies and Mycelia and Their Bioactive Compounds," J. Agricult. Food Chem. 63: 7108-7123 (2015).
Psilocybin, Wikipedia, The Free Encyclopedia (2018).
Beug et al., "Psilocybin and psilocin levels in twenty species from seven genera of wild mushrooms in the Pacific Northwest, U.S.A.", J. Ethnopharmacology, 1982, vol. 5, No. 3, pp. 271-285.
Carod-Artal, Hallucinogens in Pre-Columbian Mesoamerican Cultures Neurology, 2015, vol. 30, Issue 1, Jan.-Feb. 2015, pp. 42-49.
Chong et al., "Therapeutic Potential of Hericium erinaceus for Depressive Disorder", International Journal of Molecular Sciences, 2020, vol. 21, No. 1, 163.
De la Fuente Revenga et al., "Neurogenic potential assessment and pharmacological characterization of 6-Methoxy-1,2,3,4-tetrahydro-β-carboline (pinoline) and melatonin-pinoline hybrids", ACS Chemical Neuroscience, 2015, vol. 6, No. 5, pp. 800-810.

(Continued)

*Primary Examiner* — Christina M Borgeest
(74) *Attorney, Agent, or Firm* — Michael Best & Friedrich LLP

(57) ABSTRACT

Methods and compositions are disclosed for enhancing neurogenesis, resolving neuropathy and improving neurological health and functioning using fungal extracts and their active ingredients, including species of mushrooms and mycelia containing psilocybin and psilocin, combined with erinacines and hericenones or fungal extracts containing those active ingredients, with the addition of nicotinic acid. The compositions may optionally be combined with nervine plants.

9 Claims, No Drawings

(56) References Cited

OTHER PUBLICATIONS

Fadiman, "Might Microdosing Psychedelics Be Safe and Beneficial? An Initial Exploration", J Psychoactive Drugs, 2019, vol. 51, No. 2, pp. 118-122.

Gambaro et al., "DNA-based taxonomic identification of basidiospores in hallucinogenic mushrooms cultivated in "grow-kits" seized by the police: LC-UV quali-quantitative determination of psilocybin and psilocin", J. Pharmac. Biomed. Anal., 2016, vol. 125, pp. 427-432.

Gartz et al., "Analysis and Cultivation of Fruit Bodies and Mycelia of Psilocybe bohemica", Biochemie und Physiologie der Pflanzen, 1989, vol. 184, pp. 337-341.

Gartz et al., "Biotransformation of Tryptamine in Fruiting Mycelia of Psilocybe cubensis", Planta Med., 1989, vol. 55, No. 3, pp. 249-250.

Gartz, "Further Investigations on Pyschoactive Mushrooms of the Genera Psilocybe, Gymnopilus and Conocybe", Ann Mus Civ Rovereto, 1992, vol. 7, pp. 265-274.

Herraiz et al., "β-Carboline alkaloids in Peganum harmala and inhibition of human monoamine oxidase (MAO)", Food and Chemical Toxicology, 2010, vol. 48, No. 3, pp. 839-845.

Hutten et al., "Self-Rated Effectiveness of Microdosing With Psychedelics for Mental and Physical Health Problems Among Microdosers", Front. Psychiatry, 2019, vol. 10, Article 672, 9 pages.

Kaertner et al., "Positive expectations predict improved mental-health outcomes linked to psychedelic microdosing," Nature Sci. Rep., 2021, vol. 11, 1941.

Kim et al., "*Hericium erinaceus* (Lion's Mane) mushroom extracts inhibit metastasis of cancer cells to the lung in CT-26 colon cancer-transplanted mice", J. Agr. Food Chem., 2013, vol. 1, No. 20, pp. 4898-4904.

Kuypers et al., "Microdosing psychedelics: More questions than answers? An overview and suggestions for future research", J. Psychopharmacol., 2019, vol. 33, No. 9, pp. 1039-1057.

Lenz et al., "Identification of omega-N-Methyl-4-hydroxytryptamine (Norpsilocin) as a Psilocybe Natural Product", J. Nat. Prod , 2017, vol. 80, No. 10, pp. 2835-2838.

Mckenna et al., "Monoamine Oxidase Inhibitors in South American Hallucinogenic Plants Parts 2: Constituents of Orally-Active Myristicaceous Hallucinogens", Journal of Ethnopharmacology, vol. 12, 1984, pp. 179-211.

Mori et al., "Improving effects of the mushroom yamabushitake (*Hericium erinaceus*) on mild cognitive impairment: A double-blind placebo-controlled clinical trial", Phytotherapy Research, 2009, vol. 23, pp. 367-372.

Mori et al., "Nerve growth factor-inducing activity of Hericium erinaceus in 1321N1 human astrocytoma cells", Biological & pharmaceutical bulletin, 2008, vol. 31, No. 9, pp. 1727-1732.

Piechowska et al., "Bioactive β-carbolines in food: A review", Nutrients, 2019, vol. 11, No. 4, pp. 814.

Polito et al., A systematic study of microdosing psychedelics, 2019, PLoS One, vol. 14, No. 2, e0211023.

Riba et al., "Metabolism and disposition of N,N-dimethyltryptamine and harmala alkaloids after oral administration of ayahuasca". Drug Test Anal., 2012, vol. 4, pp. 610-616.

Stamets, "Paul Statemts: Psilocybin Mushrooms and The Mycology of Consciousness", M.A.P.S., Apr. 23, 2017, speech given, viewable on YouTube <https://www.youtube.com/watch?v=vFWxWq0Fv0U>, 3 pages.

Szigeti et al., "Self-blinding citizen science to explore psychedelic microdosing," eLife, 2021, vol. 10, e62878.

Tsai-Teng et al., "Erinacine A-enriched Hericium erinaceus mycelium ameliorates Alzheimer's disease-related pathologies in APPswe/PS1dE9 transgenic mice", J Biomed Sci, 2016, vol. 23, No. 49, 12 pages.

Tsujikawa et al., "Analysis of hallucinogenic constituents in Amanita mushrooms circulated in Japan", Forensic Science International, 2006, vol. 164(2-3), pp. 172-178.

Wronska et al., "Harman and norharman, metabolites of entomopathogenic fungus *Conidiobolus coronatus* (Entomophthorales), disorganized development of *Galleria mellonella* (Lepidoptera) and affect serotonin-regulating enzymes", PLoS One, 2018, vol. 13, No. 10, e0204828.

Yang et al., "Anti-inflammatory principles from Cordyceps sinensis", Journal of Natural Products, 2011, vol. 74, No. 9, pp. 1996-2000.

Yang et al., "Hericium erinaceus Mycelium Exerts Neuroprotective Effect in Parkinson's Disease-in vitro and in vivo Models", J Drug Res Dev, 2020, vol. 6, Issue 1, pp. 1-6.

Patel, "Recent Developments in mushrooms as anti-cancer therapeutics: a review", Biotech, 2012, vol. 3, No. 2, pp. 1-15.

Sherwood et al. "Synthesis and Biological Evaluation of Tryptamines Found in Hallucinogenic Mushrooms: Norbaeocystin, Baeocystin, Norpsilocin, and Aeruginascin," J. Nat. Prod., 2020, 83 (2): 461-467.

Zhang et al., "Erinacerins, Novel Glioma Inhibitors from Hericium erinaceus, Induce Apoptosis of U87 Cells through Bax/Capase-2 Pathway," Anticancer Agents Med. Chem., 2020, 20(17): 2082-2088 (preprint).

Latham et al., "Development of Halogenase Enzymes for Use in Synthesis", Chemical Reviews, vol. 118, 2018, pp. 232-269.

International Search Report and Written Opinion for Application No. PCT/US20/60947 dated Mar. 17, 2021 (17 pages).

Ma et al. "Hericenones and erinacines: stimulators of nerve growth factor (NGF) biosynthesis in Hericium erinaceus," Mycology, 2010, 1:2, 92-98.

Chaiyasut et al., "Anti-hyperglycemic property of Hericium erinaceus—A Mini Review", Asian Pac. J. Trap. Biomed., vol. 7, No. 11, 2017, pp. 1036-1040.

Davis et al., "Differential Immune Activating, Anti-Inflammatory, and Regenerative Properties of the Aqueous, Ethanol, and Solid Fractionsofa Medicinal Mushroom Blend", J. Inflammation Res., vol. 13, 2020, pp. 117-131.

Carhart-Harris et al., "Psilocybin with psychological support for treatment-resistant depression: an open-label feasibility study", Lancet Psychiatry, vol. 3, 2016, pp. 619-627.

Grifiths et al., "Psilocybin produces sbstantial and sustained decreases in depression and anxiety in patients with life-threatening cancer: A randomized double-blind trial", Journal of Psycho pharmacology, vol. 30, No. 12, 2016, pp. 1181-1197.

Kraehenmann et al., "Psilocybin-Induced Decrease in Amygdala Reactivity Correlates with Enhanced Positive Mood in Health Volunteers", Biological Psychiatry, vol. 78, 2015, pp. 572-581.

Nagano et al., "Reduction of depression and anxiety by 4 weeks Hericium erinaceus intake", Biomedical Research, 2010, vol. 31, No. 4, pp. 231-237.

Sarris et al., "Plant-Based Medicines for Anxiety Disorders, Part 2: A Reivew of Clinical Studies with Supporting Preclinical Evidence", CNS Drugs, 2013, vol. 27, pp. 301-319.

Ferreira et al., "Ketamine can be produced by Pochonia chlamydosporia: an old molecule and a new anthelmintic?," Parasites & Vectors, 2020, 13 (527):1-9.

Flannagan et al., Psychedelics as anti-inflammatory agents, Int. Rev. Psychiatry, 2018, 30(4): 363-375.

World Health Organization. Promoting mental health: concepts, emerging evidence, practice (Summary Report) Geneva: World Health Organization; 2004.

Prousky, "Vitamin B3 for Depression: Case Report and Review of the Literature", JOM, 2010, vol. 25, No. 3, pp. 137-147.

Grob et al., "Pilot Study of Psilocybin Treatment for Anxiety in Patients With Advanced-Stage Cancer", Arch Gen Psychiatry, 2011, vol. 68, No. 1, pp. 71-78.

Licht et al., "Simultaneous polysubstance use among Danish 3,4-methylenedioxymethamphetamine and hallucinogen users: combination patterns and proposed biological bases", Hum. Psychopharmacol. Clin. Exp., 2012, vol. 27, pp. 352-363.

DMT-Nexus, "Known substance-interactions and their effects", <https://wiki.dmt-nexus.me/Known-substance-interactions_and_their_effects>, 2013, 1 page.

\* cited by examiner

PSILOCYBIN COMPOSITIONS

CROSS-REFERENCE TO RELATED APPLICATIONS

This application is a divisional of U.S. patent application Ser. No. 16/211,281, filed on Dec. 6, 2018, which is a continuation of U.S. patent application Ser. No. 15/494,503, filed Apr. 23, 2017, which claims priority to U.S. Provisional Patent Application No. 62/365,982, filed Jul. 23, 2016, each of which is hereby incorporated by reference in its entirety.

BACKGROUND

The present invention relates to neuroregenerative compositions based upon constituents isolated from or contained within mushroom fruitbodies or mycelia, or the corresponding synthetic molecules, combined with niacin.

BRIEF SUMMARY

The current invention describes novel contributions to the field of medicinal mushroom research, particularly discoveries pertaining to neuroregeneration.

The tragedy of aging is the loss of accumulated knowledge due to neuropathy, especially related to dementia, Alzheimer's, and other neurological disorders. The cause of these disorders is a matter of dispute, ranging from free radical damage to exposure to toxins to inability of neurons to regenerate in the numbers and quality necessary for healthy mental functioning. In addressing a disease complex with multifactorial causes, offering a combination of elements that can synergistically repair and improve neurological function is an important step in helping cognitive and motor skills, in particular, as humans age and/or when exposed to neurotoxins, stress or head trauma. Not only are benefits realized from multiple active principle ingredients activating neurogenesis, but the compositions and methods below may additionally help mitigate and/or reverse ocular and cochlear nerve degeneration.

A composition including psilocybin (4-phosphoryloxy-N, N-dimethyltryptamine) or psilocin (4-hydroxy-N,N-dimethyltryptamine) in pure form or extracts from *Psilocybe* and psilocybin containing mushrooms combined with erinacines or hericenones, or extracts from *Hericium* mushroom species, and niacin (nicotinic acid or 3-pyridinecarboxylic acid, also known as vitamin B3), uniquely aids in repairing and improving neurologic functioning and signaling. Schartner et al. (2017) reported substantial increased global neural signal diversity in a psilocybin-human clinical study (Nature *Scientific Reports,* 7:46421). Additionally, niacin is known to be a neural anti-inflammatory, and, in itself, has been implicated in improving neural functioning. As niacin activates nerve endings, the inventor suggests that the addition of niacin contributes an added benefit by enhancing the neurogenic effects of psilocybin, psilocin, erinacines and hericenones by helping these nootropics cross the blood brain barrier, and migrate throughout the nervous systems, and to its end points. Moreover, niacin is a vasodilator improving blood flow in the brain by relaxing constricted blood vessels. This unique combination not only rebuilds myelin upon the axons, it also activates new astrocyte/astroglial cells and neuronalnodes of crossings such as the synaptic regions, particularly in the hippocampus. Other medicinal mushroom species also can be added, particularly species of *Antrodia, Beauveria, Copelandia, Cordyceps, Ganoderma, Grifola, Inonotus, Isaria, Panaeolus, Phellinus*, and other medicinal mushrooms and their mycelia whose unique neurogenerative properties may add benefits to this basic formulation. An excellent summary of the prior art related to the use of mushrooms as "brain foods" can be found in Phan et al. (2017), "Edible and Medicinal Mushrooms: Emerging Brain Food for the Mitigation of Neurodegenerative Diseases," *Journal of Medicinal Foods* 20(1): 1-10. Lion's Mane (*Hericium erinaceus*), Bear's Head (*H. coralloides*), or Comb Tooth (*H. ramosum*) mushrooms and mycelium have also been well studied and reported to regenerate myelin on the axons of nerves. Two particular families of compounds are most noteworthy—erinacines and hericenones. Erinacines, including known erinacines A-K, P and Q, are cyanthane terpenes isolated from the mycelia of *Hericium erinaceus* that promote NGF (nerve growth factor) synthesis. Hericenones, including known hericenones C-H, are cyanthane terpenes located in both the mycelia and fruiting body of *Hericium erinaceus* that promote NGF synthesis. Friedman et al. (2015) summarizes these activities in "Chemistry, Nutrition, and Health-Promoting Properties of *Hericium ennaceus* (Lion's Mane) Mushroom Fruiting Bodies and Mycelia and Their Bioactive Compounds," *Journal of Agricultural and Food Chemistry* 63: 7108-7123.

Although Phan et al. describes many species with potential neurogenerative properties, the psilocybin or psilocybian species (i.e. "psilocybin-containing", from the use of "psilocybienne" as described by the French mycologist, Roger Heim, with R. Gordon Wasson, in 1957 in *Les champignons hallucinogene du mexique*. Paris: Museum de historie naturelle; 1958, pp. 268-71) are not mentioned, either alone or in combinations with the edible and medicinal mushroom species described by Phan. A good summary of the role of psilocybin in humans can be found in Passie et al. (2002), "The Pharmacology of Psilocybin," *Addiction Biology* 7: 357-364. That psilocybin has neurogenerative properties was elucidated by Catlow et al. (2013), "Effects of psilocybin on hippocampal neurogenesis and extinction of trace fear conditioning," *Experimental Brain Research* 228: 481-491.

The present nootropic invention can benefit those suffering from age or trauma related neuropathologies including but not limited to tinnitus, organophosphates and other toxic compounds), heavy metals, prions, amyloid plaque formation, demyelination, nerve signaling, neurotoxic viruses, stress and numerous other agents causing neuropathies. Psilocybian mushrooms, their enzymes and their indole alkaloids may counteract and reduce the toxicity of methyl phosphonates—the core structure of Sarin, a potent neurotoxin, used in nerve gases. Moreover, the use of psilocin and psilocybin in the compositions described here may help block the neurotoxicity effects of chemical nerve toxins and lead to protecting and healing military and civilians exposed to sarin and other neurotoxic agents. The use of fungal extracts also potentially enables neurogenesis by removing agents harmful to neurological health, including but not limited to parasites such as nematodes, protozoa, pathogenic bacteria, including *Borrelia* species and other spirochetes, and other infectious organisms or viruses. The benefits of this invention to the nervous system is hard to overstate. Additional benefits are conferred not only to humans challenged with diseases or neurotoxins, but also in healthy humans, including but not limited to increased cognitive function in students, scientists, computer coders, hackers, Big Data specialists, mathematicians, astronomers, strategic planners (i.e. such as in the U.S. Defense Department), gamers, linguists, writers, futurists, Mensa members, athletes, soldiers, religious leaders, politicians, business leaders or anyone benefitting from increased memory, intelligence, imagination, cognition, clairvoyance, motor skills, spatial navigation, athleticism, ability to more quickly respond to and process stimuli, balance, neuroplasticity, state of mind, longevity and mental health. Various benefits are also expected in vertebrate animals including mammals, carnivores, omnivores, herbivores, pets including cats and dogs and companion animals, farm and produce animals, laboratory animals, zoo animals, reptiles, fish and birds. The compounds of the present invention may also be useful for bees, including those suffering from pesticides, viruses or at risk from Colony Collapse Disorder, and various other invertebrates.

DETAILED DESCRIPTION

Niacin (nicotinic acid) has long been reported to counteract the effects of psilocybin and LSD, helping those experiencing adverse reactions or "bad trips" to return to a non-psychoactive state of mind, by reversing the excitement of nerve receptors. Therefore, the prior art teaches away from using niacin to excite nerve endings using psilocybin or psilocin. Hence, counter-intuitively, this invention uniquely combines niacin with psilocin/psilocybin and erinacines/hericenones for neurological restructuring and improved neurological health. By adding niacin into a psilocybin-centered neuroregenerative nootropic nutraceutical, vitamin complex or medicine in sufficient quantities to cause extreme discomfort for those who might try to abuse a therapeutic combination containing psilocin or psilocybin, this invention provides improved methods and compositions to prevent potential abuse by those wishing to get "high." Analogous to effects of Antabuse (disulfiram), which induces an unpleasant experience for those abusing alcohol, the addition of sufficient quantities of niacin, which likewise causes extreme discomfort, with psilocybin/psilocin will help prevent the abuse of the described neurogenic formulas.

As little as 10-35 mg per day of niacin causes flushing redness on the skin, itchiness, burning and unpleasant tingling. Higher doses can lead to liver damage. 500 mg. per day is considered the top tier for safe use unless prescribed by a physician who closely monitors the patient for adverse effects. Some cholesterol-lowering products contain up to 500 milligrams of niacin and these levels can interfere with the metabolism of other medicines. 3,000 milligrams per day is clearly toxic. Upon hydrolysis, a drug called Picamilon produces GABA and niacin, allowing the inhibitory neurotransmitter GABA to pass through the blood-brain barrier. The addition of niacin to GABA to form nicotinyl-γ-aminobutyric acid or N-nicotinoyl-GABA also aids the passage of GABA across the blood-brain barrier. The stacking of niacin, psilocybin (or psilocin), GABA, erinacines and hericenones is an additional embodiment of this invention. Further embodiments include the addition of vanillic acid, trans-ferulic acid, trans-cinnamic acid, or other antiviral, anti-inflammatory polyphenols to reverse neuropathies, especially in those harmed by viruses such as, but not limited to, herpes simplex viruses (HSV), human papilloma viruses (HPV), polio, pox and other neurotoxic and inflammatory viruses.

Moreover by using psilocin or psilocybin at levels equivalent to what is colloquially known as "microdoses," i.e. <1 mg per day for a 70 kg individual, compounding effects can be realized over time. Such low doses have no noticeable consciousness altering effects on the person ingesting, and moreover, it is well know that tolerance to any perceived effects in altering one's consciousness is achieved very quickly from daily dosing of even higher levels, such as 10 mg of psilocin or psilocybin per day for a 70 kg person. Johns Hopkins researchers found the "sweet spot" for full-blown therapeutic doses to be around 35 mg of psilocybin/psilocin for a 70 kg person. (Note that psilocybin is dephosphorylated into psilocin, which passes through the blood-brain barrier.)

The term "effective amount" or "therapeutic amount" refers to an amount sufficient to have neurogenerative activity. This amount may vary to some degree depending on the mode of administration, but will be in the same general range. The exact effective amount necessary could vary from subject to subject, depending on the compound, preventative treatment or condition 10 being treated, the mode of administration, etc. The appropriate effective amount may be determined by one of ordinary skill in the art using only routine experimentation or prior knowledge in the art in view of the present disclosure. Note that effective ranges/dosages are not expected to be precisely the same for all compounds. Dosages may be optimized with each compound when the pharmacokinetics are studied to see how each compound is metabolized, which may alter the dose ranges. Nevertheless, given these factors, this neuro-enhancing invention is best managed in consultation with a skilled medical professional.

A suggested formula containing optional nervine plants that serves the purpose of neurological benefit but below any noticeable level of intoxication could be a 550 mg delivery dose via an ingestible capsule or by any means known to the art of drug delivery:

| Neurogenesis Formula 1 | |
|---|---|
| Psilocin or psilocybin | 1 mg |
| Erinacines or hericenones | 50 mg |
| Niacin per day | 200 mg |
| Extract of *Hericium erinaceus, H. corralloides, H. abietis* mycelium and/or fruitbodies of medicinal mushrooms | 199 mg |
| Extracts of plants with neurogenic properties* | 100 mg |

Plant extracts with known neuroregenerative properties include, but are not limited to: *Bacopa* species (*Bacopa monnien*), Gotu kola (*Centella asiatica*), and Gingko (*Gingko biloba*). Additional plants with anti-inflammatory properties include but are not limited to: Ginger (*Zingiber officinale*), Holy Basil (*Ocimum sanctum*), Hu Zhang (*Polygonum cuspidatum*), Oregano (*Origanum vulgare, Origanum onites*), Rosemary (*Rosmarinus officinalis, Rosmarinus eriocalyx*, species in the genus *Rosmarinus*), Turmeric (*Curcuma longa*), Green Tea (*Camellia sinensis*), lavender (*Lavandula spica* and related species in the genus *Lavandula*), skullcap (*Scutellaria lateriflora*) and oat straw (*Avena sativa, Avena byzantina*). Moreover, *Salvia divinorum*, aka Diviner's Sage, ayahuasca, a concoction made from *Banisteriopsis caapi* and *Psychotria* species, and plants containing ibogaine (*Tabemanthe iboga, Voacanga africana* and *Tabemaemontana undulate*), peyote (*Lophophora williamsil*), the seeds of morning glory (*Ipomoea tricolor* and related species) and Hawaiian baby woodrose (*Argyreia nervosa*), and Cannabis (*Cannabis sativa, C. indica* and *C. ruderalis*), can be incorporated as well. Any nervine agents from natural products may also be incorporated, including, for example, cordycepin (or *Cordyceps* extracts containing such) or amyloban (found in Lion's mane).

Depending on individual factors such as variations in metabolism, neurotransmitters and preventative treatment or condition, such a regimen of 500-1000 mg. of intake once to three times daily may produce measurable effects in one year, or the regimen may extend for up to a year or more before noticeable neurological benefits are evident. Since psilocybin converts to psilocin and is typically not detectable in the urine in 24 hours, the long term use of this nootropic formulation sustains psilocin as a serotonin agonist, while not activating dopamine receptors.

In another embodiment, the composition comprises one or more of ethyl 7-chloro-2-oxo-4-phenyl-2H-chromen-3-carboxylate, vanillic acid, chrysin, quercetin hydrate, rutin hydrate, syringic acid, trans-cinnamic acid, trans-ferulic acid, salts thereof, esters thereof, or combinations thereof, and thereby has an antiviral effect against a pathogenic virus comprising one or more of herpes *Varicella zoster* virus, Epstein-Barr virus, herpes simplex I and II viruses, human papillomaviruses (HPV), poliovirus, or viruses which contribute to neuropathies.

As ranges of these active ingredients can vary, the inventor anticipates the ranges giving benefits will include:

| Neurogenesis Formula 2 (based on a 70 kg, 154 lb person) | |
| --- | --- |
| Psilocin or psilocybin | 0.1 mg to 0.6 mg |
| Erinacines or hericenones | 1 mg to 20 mg |
| Niacin per day | 1 to 50 mg |
| Neurogenesis Formula 3 | |
| Psilocin or psilocybin | 0.6 mg to 0.9 mg |
| Erinacines or hericenones | 20 mg to 50 mg |
| Niacin per day | 50 mg to 100 mg |
| Neurogenesis Formula 4 | |
| Psilocin | 0.9 mg to 10 mg |
| Erinacines or hericenones | 50 mg to 200 mg |
| Niacin per day | 100 mg to 200 mg |
| Neurogenesis Formula 5 | |
| Psilocin or psilocybin | 0.1 mg to 10 mg |
| Erinacines or hericenones | 1 mg to 200 mg |
| Niacin per day | 1 mg to 200 mg |
| Neurogenesis Formula 6 | |
| Psilocin or psilocybin | 1 mg to 10 mg |
| Erinacines or hericenones | 50 mg to 200 mg |
| Niacin per day | 101 mg to 200 mg |
| Neurogenesis Formula 7 | |
| Psilocybin mushroom @ 1% psilocin or psilocybin | 0.1 g to 1 g |
| Lion's mane mushroom @ 1% erinacines or hericenones | 50 mg to 200 mg |
| Niacin per day | 101 mg to 200 mg |

Compounds naturally produced by the mycelium of psilocybian mushrooms and their mycelium includes baeocystin, norbaeocystin, N,N-dimethyltryptamine, 5-hydroxytryptamine (serotonin), 5-hydroxytryptophan, psilocybin and psilocin. These compounds, their precursors and immediate derivatives are candidates for neurogenesis. Synthetic or natural prodrugs, congeners and analogs of psilocybin, psilocin, baeocystin and norbaeocystin may offer similar benefits. Congeners are chemical substances related to each other by origin, structure, or function. Analogs (or analogues or structural analogs) are compounds having a structure similar to another, but differing from it in respect of a certain substituent in which one or more atoms or functional groups which are replaced with other atoms or groups or substituents. Psilocybin and psilocin prodrugs and analogs that may similarly prove useful include those where the hydroxyl group is modified or the methyl groups of the terminal amine nitrogen have been modified. Example hydroxyl group substituents include alkyl and aryl ethers and esters, for example methoxy and ethoxy ethers and acetyl esters, halogens including fluoro-, chloro- and bromo-substituents, and thio groups such as methylthio or benzothio. Example nitrogen group substituents include one or both methyl groups substituted with ethyl, propyl, isopropyl, butyl, isobutyl, secbutyl, tertbutyl, amyl or allyl groups and the N-trimethyl analogs. The corresponding phosphate esters, namely psilocybin and baeocystin analogs, may also prove useful, as may analogs where one or more hydrogen atom is replaced by fluorine, chlorine or bromine. Also preferred, where possible, are the salts of the tryptamine compounds, for example hydrochloride, fumarate, maleate, picrate, oxalate, tartrate and sulfate salts, which are typically more stable. Also preferred are the zwitterionic forms, particularly of the phosphate esters and quaternary ammonium compounds. Preferred analogs include: 4-acetoxy-N,N-dimethyltryptamine (4-AcO-DMT or O-acetylpsilocin) the acetylated form of the psilocin (4-OH-DMT). It is a possible prodrug of psilocin (as are other 4-alkyl-esters), more stable than psilocin, and has a longer shelf life; 4-acetoxy-N-methyl-N-ethyltryptamine (4-AcO-MET), a psilocin analog substituted at $R_4$ of its indole heterocycle with an acetoxy (AcO or $CH_3COO^-$) functional group which also contains a methyl group and an ethyl chain bound to the terminal amine nitrogen of its tryptamine backbone. 4-AcO-MET is an acetate ester analog of 4-OH-MET and a N-substituted ethyl homolog of 4-AcO-DMT; 4-acetoxy-N,N-diethyltryptamine (4-AcO-DET); 4-acetoxy-N-methyl-N-propyltryptamine (4-AcO-MPT); 4-acetoxy-N-methyl-N-isopropyltryptamine (4-AcO-MIPT); 4-acetoxy-N,N-dipropyltryptamine (4-AcO-DPT) and 4-acetoxy-N,N-diisopropyltryptamine (4-AcO-DI PT); 4-hydroxy-N-methyl-N-ethyltryptamine (4-OH-MET, metocin or methylcybin), a 4-hydroxy N-substituted structural analog of psilocin and the with a methyl and an ethyl group bound to the terminal amine nitrogen of the tryptamine structure; 4-hydroxy-N-methyl-N-propyltryptamine (4-OH-MPT); 4-hydroxy-N-methyl-N-isopropyltryptamine (4-OH-MI PT); 4-hydroxy-N,N-diethyltryptamine (4-OH-DET); 4-hydroxy-N,N-dipropyltryptamine (4-OH-DPT); 4-hydroxy-N,N-diisopropyltryptamine (4-OH-DI PT); and 4-hydroxy-N,N-diallyltryptamine (4-OH-DALT); analogs where the 4-OH group has been removed, such as N,N-dimethyltryptamine (DMT), N-methyl-N-ethyltryptamine (MET), N-methyl-N-propyltryptamine (MPT), N,N-diethyltryptamine (DET), N,N-dipropyltryptamine (DPT), N,N-isopropyltryptamine (DIPT), N-methyl-N-isopropyltryptamine (MI PT), α-methyltryptamine (AMT), N-ethyl-N-isopropyltryptamine (EIPT), N-methyl-N-butyl-typtamine (MBT) or analogs substituted at other positons such as N,N-dimethyl-5-hydroxytryptamine (5-OH-DMT or bufotenine), 5-methoxy-a-methyltryptamine (5-MeO-aMT), 5-methoxy-N,N-dimethyltryptamine (5-MeO-DMT), 5-methoxy-N,N-diethyltryptamine (5-MeO-DET), 5-methoxy-N,N-dipropyltryptamine (5-MeO-DPT), 5-methoxy-N,N-diisopropyltryptamine (5-MeO-DIPT), 5-methoxy-N-ethyl-N-isopropyltryptamine (5-MeO-EIPT), 2,α-dimethyltryptamine (2,α-DMT), α,N-dimethyltryptamine (α,N-DMT), α-ethyltryptamine (α-ET), 2-methyl-N,N-dimethyltryptamine (2-Me-DMT), 2-methyl-N,N-diethyltryptamine (2-Me-DET), 1-methylpsilocin and ibogaine (a complex tryptamine). In general, equimolar amounts of an analog may be used in place of psilocybin and/or psilocin in the formulas above, or amounts producing equivalent functional effects may be utilized. See *TiHKAL: The Continua-*

*tion* by Alexander Shulgin and Ann Shulgin (1997, Transform Press) for an in-depth discussion of both "legal" analogs and "chemical" analogs, and synthesis and effects of various psilocybin and psilocin analogs.

Additional pharmaceutical excipients useful for the compositions as described herein include, for example, the following: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, asorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolau rate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

Another embodiment is methods for manufacturing a dosing form for treating, ameliorating, mitigating, alleviating, reducing and curing a nerve damage from neurotoxic virus infection comprising: formulating a composition into a dosage form comprising sprays, capsules, tablets, elixirs, emulsions, lozenges, suspensions, syrups, pills, lotions, epidermal patches, suppositories, inhalers, or injectables. Any methods known to the art for formulating extracts or active principal ingredients into lotions, soaps, etc. may be utilized.

Using blue light stimulation in the 280-400 nm wavelength range, precursor molecules to psilocybin and psilocin production can be elicited from the mycelium, primordia or fruitbodies of psilocybian or their close non-psilocybian relatives, to induce the formation of neurogenic compounds, including those that are not illegal, and therefore would not violate statutes in the United States or other countries. The goal here is to employ legal neurogenic precursor, congener or analog compounds related to psilocybin and psilocin.

Induction of bioactive compounds from mycelium through light stimulation is a method that can be used for discovering synergistic neurogenic compounds. Blue light activates shikimic acid production in mycelium, and antioxidant polyphenols, while also stimulating tyrosinase leading to melanization while inhibiting laccase and other enzymatic pathways, simultaneously inducing the production of psilocin, psilocybin and other tryptamines from mycelium in psilocybin active mushrooms and their relatives. Modifying the wavelength (i.e. blue light for 12 hours, red light for 12 hours, per day) and frequency of light exposure, including "pulsing" of the light, can help articulate the expression of active neurogenic ingredients. The shikimic acid pathway gives rise to aromatic amino acids (phenylalanine, tyrosine and tryptophan), which are precursors for the formation of ergot alkaloids, lysergic acid, psilocybin and psilocin (Isaac, *Fungal-Plant Interactions*, Springer Netherlands, 1992). The inventor postulates that light stimulation evoking the transformation of ergosterol to vitamin D will also influence the pathways where light induces neurogenic compounds from mycelium. These pathways are interrelated and can be used for creating medically significant novel compositions whose synergy is useful for repairing the neuropathic damage by promoting neurogenesis and synaptic integrations. Exposure of mycelium to select wavelengths of light, especially blue and red spectra, may induce indole alkaloids related to psilocin analogues that have distinct antiviral and neuroprotective properties.

The biosynthesis of psilocybin from tryptophan involves enzymatic decarboxylation, methylation at the N9 position, 4-hydroxylation and O-phosphorylation. Light stimulation triggers the production of psilocybin and psilocin in the mycelium of, for instance *Psilocybe azurescens, Psilocybe cyanescens* and *Psilocybe cubensis*, possibly by stimulation of the enzymatic reactions. The "off/on" production of psilocybin, psilocin, baeocystin (the N-demethylated analog of psilocybin, 4-phosphoryloxy-N-methyltryptamine), norbaeocystin (the N-demethylated analog of psilocin, 4-phosphoryloxy-tryptamine) and other associated alkaloids from the mycelium caused by light exposure (particularly UV) are interrelated to the production of p-coumaric acid and the resultant metabolic expression of tyrosinase coding for melanin, especially prior to, during and after the time of primordia formation. The transition of the mycelium upon controlled light exposure, especially blue and UV light in the 280-420 nanometers ranges, affords the development of a customized suite of active ingredients, from which an extract be created or combined with active pharmacological molecules for a net benefit for the patient that consumes this unique combination.

Compositions and methods utilizing combinations of psilocin or psilocybin, and their immediate precursors, derived from mycelium that is exposed to light, particularly in the blue spectrum, additionally combined with erinacines or hericenones, with or without the addition of niacin, can result in medically significant, deliverable formulations for human consumption supporting neurogenesis.

This inventor reported *Psilocybe azurescens* to be the most potent psilocybian mushrooms in the world. (Stamets, P., *Psilocybin Mushrooms of the World,* 1996, Ten Speed Press.) A common side effect of taking this psychoactive mushroom species is loss of coordination and in some occasions, temporary paralysis. This mushroom contains ingredients related to psilocybin that may swamp receptor fields to cause these conditions. In medicine, the difference between a toxin and a medicine is often the dose. As such, this inventor suggests that other potent neurologically active ingredients are within *Psilocybe azurescens* (and to a lesser degree, *Psilocybe cyanescens* and *Psilocybe subaeruginosa*), which are likely useful for neurogenesis when presented or isolated at proper dosages.

Exposing mycelium grown on rice to blue and ultraviolet light in the 280-420 nanometer wavelengths, for a short window of time, lasting for a short duration of only 1-5 days, can help create and potentiate the neuroregenerative agents described herein. The intensity of light can range from 50-1,000 lux. By incubating the sterilized rice being actively colonized by the mycelium in plastic bags, which have grown out for a minimum of 1 week and up to 16 weeks, UV light exposure lights can be placed directly above and below horizontally shaped bags for maximum light exposure. The plastic bags or glass vessels can be selected for allowing these blue light wavelengths to reach the mycelium. The mycelium can undergo a phase-change in response to light stimuli into producing derivative neuroregenerative agents (it is to be expected that during this transitional period, the mycelium may contain varying mixtures of active compounds). This method and derivative improvements can potentiate the production of neuroregenerative molecules, some of which are intermediates during the melanization pathways activated by light exposure at specific wavelengths. This opens possibilities for customizing the output of specific active molecules using precise wavelengths, exposure times and intensities of light for manufacturing and potentiating production from mycelium. Lights can be pulsed and/or sequenced with varying wavelengths for exposing mycelium. The mycelium can also be subsequently agitated to cause new growth spurts, causing differentiation of hyphae with multiple nuclei per cell and hyper-expression of extracellular metabolites. Moreover, active molecules may be emitted differentially over time, allowing for windows of harvesting by washing the mycelium using cold EtOH and $H_2O$ or other solvents and processes known to the art of natural product extraction.

Serotonin is the fundamental neurotransmitter all animals use. That serotonin and psilocybin co-occur within psilocybin-containing ("psilocybian" as used herein) mushrooms, and that psilocybin is a serotonin agonist, substituting for serotonin in the human brain and exciting neurotransmission, underscores the value of exploring these pathways for neurogenic compounds. Utilizing specific wavelengths of light—both blue and red spectra—can induce or suppress expression of these compounds, allowing customization of neurogenic compounds which can be useful medically. Exposure of red light spectra on maturing mycelium of psilocybin active mushroom species—which naturally would generate psilocybin and psilocin in its mycelium—can be used to acquire compounds useful for neurogenesis.

Moreover, this unique combination of compounds can be incorporated into therapies with such combinations providing unique advantages for medically significant advancements in repairing neurons, removing amyloid plaques, improving mental health, including reducing depression, anxiety, or substance abuse, improving cognition or agility, and improving overall the ecology of consciousness. The inventor foresees utilizing such compounds in helping amputees activate their articulable prostheses. Such derivatives can help the improve cyborg technologies, allowing for neurons to grow into and mesh computer interfaces.

Moreover, the production of active principle ingredients from mycelium can be additionally enhanced by vibrational actions, including but not limited to pulsed sonic vibration—sonification—in combination with active principal ingredients stimulating UV wavelengths. Specific UV spectra and vibrations can be customized for enhancing yields.

Psilocybin dephosphorylates into psilocin in the liver, which then passes through the blood-brain barrier. Subsequent to enzymatic conversion and liver metabolism, psilocin is further degraded along at least one pathway, one rendition of which is featured below. These derivative compounds have neurogenic potential and are anticipated to be useful in nootropic formulations.

Adapted from Psilocybin, Wikipedia, The Free Encyclopedia.

Moreover, since psilocin and its analogs are neurotransmitters, and substitute for serotonin, acting as an agonist exciting serotonin receptors, their ability to enhance neurotransmission while in combination with nerve growth factors such as erinacines and hericenones, provides a unique opportunity for spurring neurogenesis. When combined with niacin, which causes nerve ending excitement, and additionally combined with mushroom and plant extracts, compounded neurogenic benefits are anticipated by this inventor.

The inventor claims rights to obvious embodiments of this invention, including using delivery systems, compositions, combinations and solvent extraction methods as outlined in this author's previous patents and patent applications, which are a matter of record at the United States Patent and Trademark Office as well as methods and compositions known to the art of pharmaceutical science and drug discovery.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations

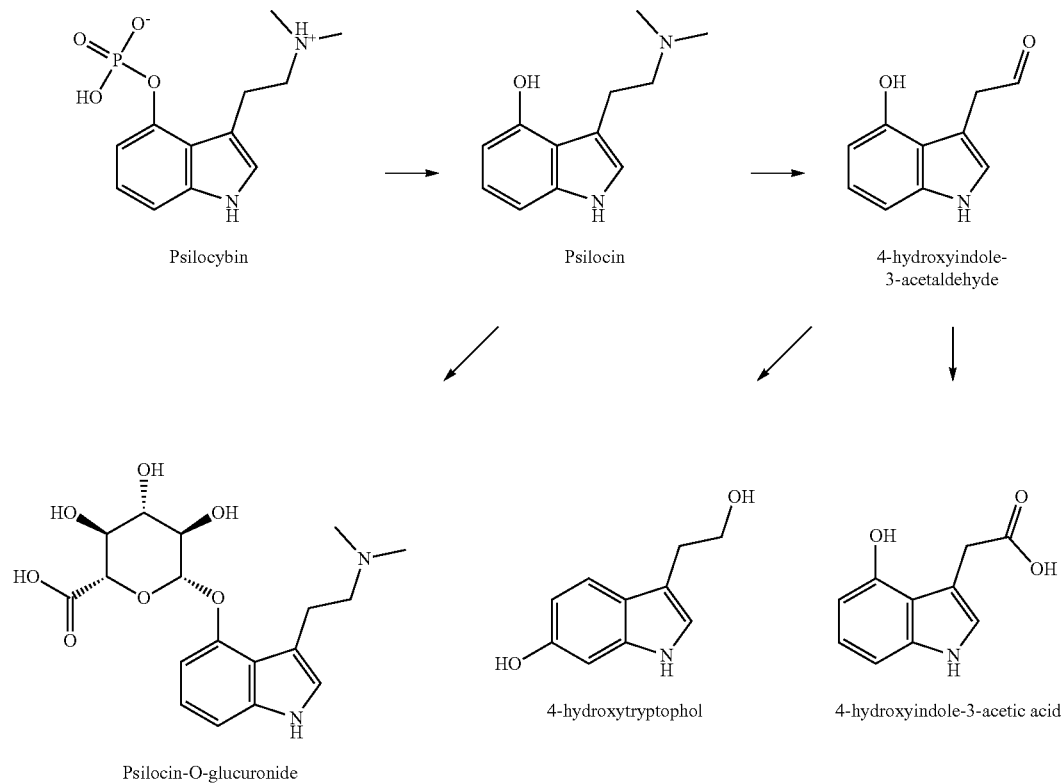

described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

No limitations with respect to the specific embodiments and examples disclosed herein are intended or should be inferred, as the examples and embodiments are representative only. While examples and preferred embodiments of the present invention have been shown and described, it will be apparent to those skilled in the art, or ascertainable using no more than routine experimentation, that many changes and modifications may be made without departing from the invention in its broader aspects. The appended claims are therefore intended to cover all such changes, modifications and equivalents as fall within the true spirit and scope of the invention.

The invention claimed is:

1. A composition comprising:
    0.1 mg to 10 mg of psilocybin or psilocin;
    an extract of *Hericium erinaceus* comprising 50 mg to 200 mg of erinacines or hericenones; and
    199 mg of one or more medicinal mushroom species of *Inonotus* mycelia, fruitbodies, mycelial extracts, fruitbody extracts, or combinations thereof.

2. The composition of claim 1, wherein the composition further comprises niacin.

3. The composition of claim 1, wherein the composition further comprises one or more of: mycelia, fruitbodies, mycelial extracts, or fruitbody extracts of fungi selected from the group consisting of *Antrodia, Beauveria, Copelandia, Cordyceps, Ganoderma, Grifola, Hericium, Isaria, Panaeolus, Phellinus* or combinations thereof.

4. The composition of claim 1, wherein the composition further comprises neurotropic or nootropic fungal or plant extracts.

5. The composition of claim 1, wherein the composition further comprises one or more extracts of: *Bacopa monnieri, Centella asiatica, Gingko biloba, Zingiber officinale, Ocimum sanctum, Polygonum cuspid atum, Origanum vulgare, Origanum onites, Rosmarinus* species, *Curcuma longa, Camellia sinensis, Lavandula* species, *Scutellaria lateriflora, Avena sativa, Avena byzantine, Salvia divinorum, Banisteriopsis caapi, Psychotria* species, *Tabemanthe iboga, Voacanga africana, Tabemaemontana undulate, Ipomoea tricolor, Argyreia nervosa, Cannabis sativa, Cannabis indica, Cannabis ruderalis*, or combinations thereof.

6. A composition comprising:
    0.1 to 10 mg of psilocybin or psilocin;
    an extract of *Hericium erinaceus* comprising 50 mg to 200 mg of erinacines or hericenones;
    199 mg of one or more medicinal mushroom species of *Inonotus* mycelia, fruitbodies, mycelial extracts, fruitbody extracts or combinations thereof, and
    niacin.

7. The composition of claim 6, wherein the composition further comprises one or more of: mycelia, fruitbodies, mycelial extracts, or fruitbody extracts of fungi selected from the group consisting of *Antrodia, Beauveria, Copelandia, Cordyceps, Ganoderma, Grifola, Hericium, Isaria, Panaeolus, Phellinus* or combinations thereof.

8. The composition of claim 6, wherein the composition further comprises neurotropic or nootropic fungal or plant extracts.

9. The composition of claim 6, wherein the composition further comprises one or more extracts of: *Bacopa monnieri, Centella asiatica, Gingko biloba, Zingiber officinale, Ocimum sanctum, Polygonum cuspid atum, Origanum vulgare, Origanum onites, Rosmarinus* species, *Curcuma longa, Camellia sinensis, Lavandula* species, *Scutellaria lateriflora, Avena sativa, Avena byzantine, Salvia divinorum, Banisteriopsis caapi, Psychotria* species, *Tabemanthe iboga, Voacanga africana, Tabemaemontana undulate, Ipomoea tricolor, Argyreia nervosa, Cannabis sativa, Cannabis indica, Cannabis ruderalis*, or combinations thereof.

* * * * *